(12) United States Patent
Saadat

(10) Patent No.: US 7,232,458 B2
(45) Date of Patent: *Jun. 19, 2007

(54) APPARATUS AND METHODS FOR COOLING A REGION WITHIN THE BODY

(75) Inventor: Vahid Saadat, Saratoga, CA (US)

(73) Assignee: Nidus Medical, LLC, Saratoga, CA (US)

( * ) Notice: Subject to any disclaimer, the term of this patent is extended or adjusted under 35 U.S.C. 154(b) by 26 days.

This patent is subject to a terminal disclaimer.

(21) Appl. No.: 10/841,160

(22) Filed: May 7, 2004

(65) Prior Publication Data
US 2004/0210286 A1    Oct. 21, 2004

Related U.S. Application Data

(63) Continuation of application No. 10/159,713, filed on May 31, 2002, now Pat. No. 6,746,474.

(51) Int. Cl.
*A61F 7/00* (2006.01)
(52) U.S. Cl. .................. 607/105; 607/104; 607/113
(58) Field of Classification Search .......... 607/96, 607/104, 105, 106, 113
See application file for complete search history.

(56) References Cited
U.S. PATENT DOCUMENTS

| | | | |
|---|---|---|---|
| 4,719,919 A | 1/1988 | Marchosky et al. | |
| 5,531,776 A * | 7/1996 | Ward et al. | 607/105 |
| 5,531,778 A | 7/1996 | Maschino et al. | |
| 5,540,730 A | 7/1996 | Terry, Jr. et al. | |
| 5,571,150 A | 11/1996 | Wernicke et al. | |
| 5,707,400 A | 1/1998 | Terry, Jr. et al. | |
| 5,733,319 A * | 3/1998 | Neilson et al. | 607/105 |
| 5,840,070 A | 11/1998 | Wampler | |
| 5,861,022 A * | 1/1999 | Hipskind | 607/109 |
| 5,876,422 A | 3/1999 | van Groeningen | |
| 6,012,457 A | 1/2000 | Lesh | |
| 6,017,337 A | 1/2000 | Pira | |
| 6,139,569 A | 10/2000 | Ingle et al. | |
| 6,164,283 A | 12/2000 | Lesh | |
| 6,238,421 B1 | 5/2001 | Gunther et al. | |
| 6,248,126 B1 | 6/2001 | Lesser et al. | |
| 6,364,899 B1 | 4/2002 | Dobak, III | |
| 6,589,271 B1 | 7/2003 | Tzeng et al. | |

\* cited by examiner

*Primary Examiner*—Roy D. Gibson
(74) *Attorney, Agent, or Firm*—Levine Bagade Han LLP (57) ABSTRACT

Apparatus and methods for cooling selected regions within a body are described herein. An implantable cooling system is used to cool regions of the brain, spinal cord, fibrous nerve bodies, e.g., vagus nerve, etc. down to about 30° C. to diminish nerve impulses which control seizures or chronic pain. The system includes an implantable unit containing a pumping mechanism and/or various control electronics. It also has a heat exchanger attachable to a tubular body organ, such as the superior vena cava or the inferior vena cava, through which the heat is effectively dissipated. Also included is a heat pump such as a Peltier junction configured to be placed into contact with the region of tissue to be cooled. The heated portion of the Peltier junction is cooled by a liquid heat transfer medium which absorbs the heat from the junction and dissipates it into the tubular body organ.

35 Claims, 8 Drawing Sheets

APPARATUS AND METHODS FOR COOLING A REGION WITHIN THE BODY

CROSS-REFERENCE TO RELATED APPLICATIONS

This is a continuation of U.S. patent application Ser. No. 10/159,713 filed May 31, 2002, now U.S. Pat. No. 6,746,474, which is incorporated herein by reference in its entirety.

TECHNICAL FIELD OF THE INVENTION

The present invention relates to the controlled cooling of selected regions within a body for the purpose of controlling pain. The present invention relates to the cooling of selected regions within the body, such as the vagus nerves, by implantable apparatus for reducing pain sensation or stimulating the nerves.

BACKGROUND OF THE INVENTION

It is generally known that cooling an injured region of the body typically helps to abate the associated pain. For example, cooling painful joints, inflamed tissue, or burned areas of skin can help with reducing the pain and inflammation. However, this type of treatment is generally limited to cooling via the surface of the skin, e.g., by applying a cold compress or ice, and is not optimal in limiting the area to be treated.

Other methods of pain management usually include the ingestion or intake of analgesics or other anodynes. For instance, chronic pain typically associated with conditions such as muscle spasms, tendonitis, sciatica, etc., is not only very painful to the individual, but is usually very difficult to treat and can lead to debilitating conditions.

Such conditions, e.g., muscle spasms, may be painful, violent, and involuntary and affect a large segment of the population. This type of pain is often also chronic, i.e., lasts for one day or longer. Other conditions may result from injury or trauma to affected region within the body, such as to the muscles or to the nerves that innervate the muscles.

Examples of other painful conditions include sciatica and tendonitis. Sciatica is a condition characterized by pain radiating from the muscles in the back into the buttocks and may be a result of trauma to the spinal cord or to the sciatic nerve.

The debilitating effects of chronic pain are not only a source of anxiety and distress for the individual, but also represent a tremendous cost to society. For instance, workers suffering from chronic pain are frequently absent from work for weeks or even longer. This poses a great expense not only to the employer in sick-time coverage and disability pay, but also to society in lost productivity.

A variety of medicines are typically used in an attempt to alleviate the conditions associated with chronic pain. These have included muscle relaxants, such as methocarbamol, carisoprodol, mephenesin, etc. Nonsteroidal anti-inflammatory agents, such as ibuprofen, aspirin, and indomethacin are also used in conjunction with muscle relaxants for treating muscle spasms, tendonitis and sciatica. However, these methods provide, at most, partial relief and do not provide the type of relief considered adequate by most people. Accordingly, there exists a need for a method of effectively alleviating chronic pain and doing so in a manner which least impacts a person's normal daily activities.

These types of conditions may potentially be treated by the stimulation of certain regions within the brain or certain nerve fibers leading to and from the brain. One such nerve is the vagus nerve, which is located in the side of the neck and acts as a highway of information for carrying messages to and from the brain. The vagus nerve is connected to many areas of the brain which are involved in detecting chronic pain as well as areas which are instrumental in producing seizures and spasms, such as those symptoms associated with Parkinson's disease and epilepsy.

The treatment of internal organs and regions within the body to bring relief have sometimes involved electrical or hyperthermic treatments. For instance, treatment modalities have included delivering energy, usually in the form of RF or electrical energy, for the heating of, e.g., malignant tumors. But many of these treatments are performed through invasive surgery (laparoscopic or otherwise) that may require repeated procedures to achieve the desired effect.

Methods used in treating epilepsy include vagal nerve stimulation, where the vagal nerve is electrically stimulated to disrupt abnormal brain activity. This may include implanting an electrical stimulation device within a patient that is electrically connected to a portion of the vagal nerve. However, this method of treatment is limited to epilepsy and does may not be effective in the treatment of other types of disorders.

SUMMARY OF THE INVENTION

Various devices and methods for cooling selected regions within a body are described herein. For example, an implantable cooling system used to cool regions of the brain, regions of the spinal cord, fibrous nerve bodies such as the vagus nerve which relay impulses from the brain which may take part in epilepsy, Parkinson's disease, chronic pain impulses, etc. Other regions of the body for cooling may include tissue and fibrous material as well. Cooling these certain regions within the body from about 37° C. down to about 30° C. aids in diminishing or masking these impulses to control seizures or chronic pain.

Such an implantable cooling system may comprise an implantable unit that may contain a pumping mechanism and/or various control electronics. It may also include a heat exchanger connected to a heat sink contained within the body or that may be a part of the body. Such a heat sink preferably includes tubular body organs through which heat may be effectively dissipated, such as the superior vena cava (SVC) or the inferior vena cava (IVC) because of the relatively high blood flow rate therein.

Additionally, the cooling system may comprise a variety of cooling devices, but it is preferably an electrically controllable thermoelectric module that may essentially function as a heat pump. Such modules are typically known as Peltier junctions and are generally comprised of a sandwich of at least two dissimilar metals. When an electric current is applied to such a module, heat is moved from one side of the module to the other, thereby creating a "cool" side due to the Peltier Effect and a converse "hot" side due to the Seebeck Effect. Despite the reversible polarity of the current and the resulting reversible heating and cooling effect, the side contacting the nerve body below is called the cooled region, and conversely the side which is heated is called the heated region for simplicity. It is the cooled region which may be placed into intimate contact with the various regions within the body to effect the cooling of the appropriate tissue.

The heated region may be placed in thermal contact with a heat exchanging chamber filled with a liquid heat transfer medium. The liquid heat transfer medium is preferably a fluid which has a high specific heat capacity and is also biocompatible. Such fluids may include chilled saline, fluorinated hydrocarbon (Fluorinert™), liquid chlorodifluoromethane, water, etc., among others. As the heat transfer medium absorbs the heat from the heated region, the medium may be urged by a pump to pass through a controllable outlet and through a feedline to the second heat exchanger, where the absorbed heat may be discharged to the SVC, IVC, or other body organ.

The cooling device or unit may comprise a variety of configurations. One configuration is a semi-circular configuration where the cooled region is circumferentially surrounded by the heated region. Each of the cooled and heated regions may define an opening through which the vagus nerve or other nerve body to be cooled may pass through to enable the junction to fixedly attach about the nerve. To effect a better heat transfer coefficient between the junction and the nerve body, biocompatible adhesives having a sufficient thermal conductivity, i.e., does not impede the heat transfer, may be used as a thermal interface between the two. Other configurations may include clamping members which may be urged open to allow for placement onto the nerve body, and helical variations which may be unraveled temporarily by an external force to allow for placement around the nerve body. Upon releasing the external force, the device may preferably reconfigure itself to reform its helical configuration and wrap around the nerve body.

The pump may be a conventional implantable pump with an integrated power supply and/or control electronics. Alternatively, the power supply to actuate the pump and cooling unit may be supplied by an implantable transcutaneous charger. Such a charger may have its power supply recharged by an external charging unit which may be placed over the skin in proximity of the charger. Other types of pumps may be subcutaneously implanted and externally actuated and driven. Such pumps may have a diaphragm attached to an actuator, which may comprise a permanent magnet, in the pumping chamber. The diaphragm and pump may then be actuated by an external alternating electromagnet placed over the skin. Other types of pumps may also include rotational pumps that are subcutaneously implanted and also externally actuated.

The heat exchangers which may be in contact with the tubular body organs may be configured in a variety of ways. Functionally, a heat exchanger which maximizes the contact surface area between the exchanger and the body organ is desirable. Also, the exchanger is also preferably configured to hold onto the tubular body organ without damaging the tissue in any way. Such configurations may include a cuff-type design in which a heat exchanger element may be configured into a looped or alternating manner to increase the surface area traversed by the fluid medium as it travels through the cuff. Alternatively, the cuff may define a single continuous heat exchange chamber through which the fluid medium may fill before exiting through an outlet line and back to the cooling unit. The heat exchanger cuff, as well as the other portions of the cooling system, are preferably made from a biocompatible metal or alloy, e.g., stainless steel, nickel titanium, etc.

Alternatively, a combination implantable pump and heat transfer device may also be used in the cooling system. This variation may comprise an injectable pump having a dual-chambered body, e.g., an aspiration and an irrigation chamber. The chambers may be accessible through the patient's skin by insertion of a multi-lumened catheter having at least one lumen in fluid connection with the aspiration chamber and at least one lumen in fluid connection with the irrigation chamber. When the cooling system is to be actuated, the catheter may be inserted through the skin and the heated or charged fluid medium may be drawn into the aspiration chamber and up into the lumen while cooled fluid medium may be pumped or urged into the irrigation chamber and into the system via the other lumen.

The fluid lines transporting the fluid medium through the cooling system may comprise separate lines for the heated or charged fluid and the cooled fluid medium. Alternatively, a single multi-lumened line may define separate fluid lines therein as well as additional access lumens to carry the electrical, control, and/or power lines to minimize the number of separate lines running between units of the cooling system. The lines may be made from a variety of conventionally extrudable or formable materials, e.g., silicone, polyethylene (PE), fluoroplastics such as polytetrafluoroethylene (PTFE), fluorinated ethylene polymer (FEP), perfluoroalkoxy (PFA), and thermoplastic polymers, such as polyurethane (PU), etc.

Moreover, to prevent any kinking or undesirable bending of the fluid lines when implanted within a body, the lines may be reinforced by wrapping, braiding, or surrounding them with various metals or alloys, as is well known in the catheter arts. Examples of such metals and alloys include stainless steels, nickel titanium (Nitinol) alloys having superelastic alloy characteristics, and other superelastic alloys. Additionally, the fluid lines may also be surrounded by insulative materials to minimize any undesirable heat transfer from or to the fluid medium contained therein.

DETAILED DESCRIPTION OF THE INVENTION

Figure 1:
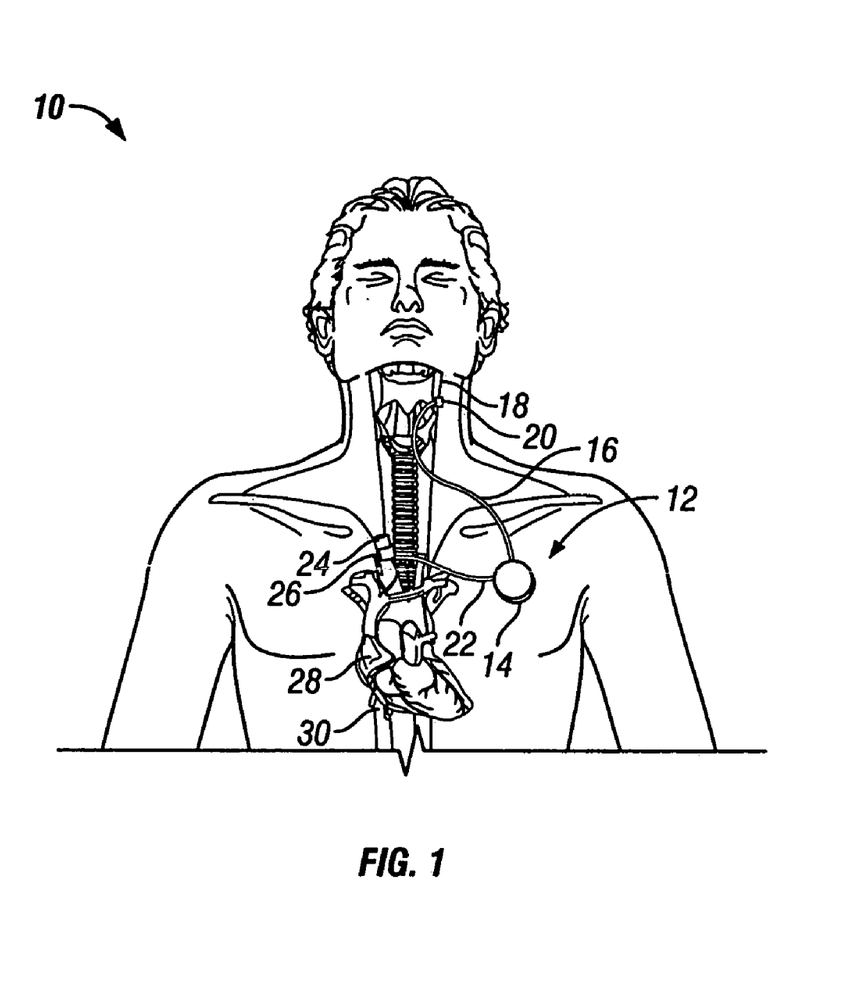
FIG. 1 shows a diagram of a variation of the cooling device implanted within a body and attached to the superior vena cava and a vagal nerve.

Devices and methods for the controlled cooling of selected regions within a body are described herein. FIG. 1 shows a representative illustration of a patient 10 having a variation of cooling system 12 implanted within the body. The shown variation of system 12 may comprise an implantable unit 14 thermally connected via coolant feedline 16 to cooling unit 20, which is preferably in intimate contact with a fibrous nerve body 18, such as the vagus nerve. Implantable unit 14 may be coated with any variety of biocompatible polymer or it may have a housing made from a biocompatible metal or alloy, such as stainless steel. Unit 14 may contain a pump, electronics for controlling the system 12, a power supply, and/or any combinations thereof, as will be discussed in further detail below. The unit 14 may be implanted in various locations within the body relative to heart 28 and is further thermally connected via coolant feedline 22 to heat exchanger 26. Heat exchanger 26 is preferably in thermal or heat conductive contact with a tubular body organ through which heat may be effectively dissipated, such as the superior vena cava (SVC) 24, as shown in the figure, or inferior vena cava (IVC) 30 or other large vascular members.

In operation, nerve body 18 may be cooled from normal body temperature, about 37° C., preferably down to about 30° C., by cooling unit 20. The cooling unit 20 may be comprised of a variety of cooling devices, but it is preferably an electrically controllable thermoelectric module that functions to remove heat from nerve body 18 and the region near it, much in the way a heat pump functions. One such module is a Peltier junction, a device generally comprised of a sandwich of at least two carefully chose dissimilar metals, alloys, or intermetallic compounds. When an electric current is applied to such a module, heat is moved from one side of the module to the other, thereby creating a "cool" side due to the Peltier Effect and a converse "hot" side due to the Seebeck Effect. If the polarity of the current were reversed, the opposite effect would occur in the respective sides of the module. The side undergoing the Peltier Effect (or "cool" side) may be made, for instance, from bismuth telluride ($Bi_2Te_3$) and the side undergoing the Seebeck Effect (or "hot" side) may be made from lead telluride (PbTe), silicongermanium (SiGe), or also $Bi_2Te_3$. To ensure biocompatibility when implanted, the metals or alloys of cooling unit 20 are preferably made of biocompatible materials. Some of the advantages of using a thermoelectric module include the lack of moving parts, lack of vibration and noise, small sizes and configurable shapes, as well as a long module life and precise temperature control, etc. Despite the reversible polarity of the current and the resulting reversible heating and cooling effect, the side contacting the nerve body below is called the cooled region, and conversely, the side which is heated is called the heated region for simplicity.

Figure 2:
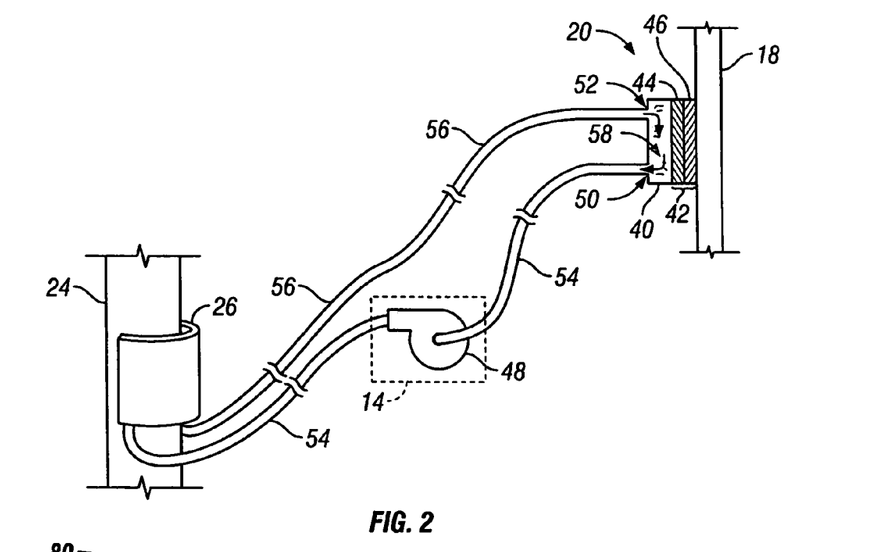
FIG. 2 shows a representative schematic of a variation on the cooling device with a pump.

As shown in the representative schematic seen in FIG. 2 of a variation on the cooling device, Peltier junction 42 preferably takes advantage of cooled region 46 by being placed in close contact against or around nerve body 18. As cooled region 46 is cooled, heated region 44 conversely heats up. Heat exchanger 40, which may be formed as a chamber filled with a liquid heat transfer medium 58, is formed to be in thermal contact with heated region 44. The liquid heat transfer medium 58 is preferably a fluid which has a high specific heat capacity and is also biocompatible. Such fluids may include chilled saline, fluorinated hydrocarbon (Fluorinert™), liquid chlorodifluoromethane, water, etc., among others. A pump 48 is preferably held within implantable unit 14 and is fluidly connected via coolant feedline 54 to cooling unit 20. As heat transfer medium 58 absorbs the heat from heated region 44, medium 58 may be urged to pass through a controllable outlet 50 through feedline 54 and through implantable unit 14 by pump 48. From pump 48, the heated medium 58 may then continue to travel through feedline 54 to heat exchanger 26, where the absorbed heat may be discharged.

Heat exchanger 26 is preferably in intimate contact with a hollow body organ which is able to act as a heat sink and absorb the heat which may be discharged from medium 58 as it flows through heat exchanger 26. Heat exchanger 26 is preferably made from a biocompatible metal or alloy, e.g., stainless steel, which has an adequate thermal conductivity value such that heat from medium 58 may be effectively transferred through exchanger 26 and into the hollow body organ to which it is contacting. Hollow body organs which generally have a high blood flow rate and which may functionally act as heat sinks may include SVC 24, as shown in the figure. Heat exchanger 26 may be configured such that it intimately covers a portion of SVC 24 substantially around its circumference, i.e., around at least a majority of the circumference of SVC 24, and it may be formed in a cuff-shaped configuration such that it securely clamps around the hollow body organ to prevent excessive movement or dislodgment. Additionally, a biocompatible adhesive which has an effective thermal conductivity value may be filled between heat exchanger 26 and SVC 24 to aid in optimizing heat transfer and attachment to SVC 24.

Alternatively, rather than having heat exchanger 26 contacting SVC 24, it may instead be placed at a location just beneath or close to the skin. During the heat exchanging process, the fluid medium 58 flowing through implanted exchanger 26 may then be cooled by external methods, such as simply placing a cooling device like a package of ice over the skin adjacent to the implanted exchanger 26. Once the fluid medium 58 has had its heat energy sufficiently discharged, it may then flow back through coolant return line 56 to cooling unit 20, where fluid medium 58 may pass through an optionally controllable inlet 52 into heat exchanger 40 to begin the process again.

Figure 3:
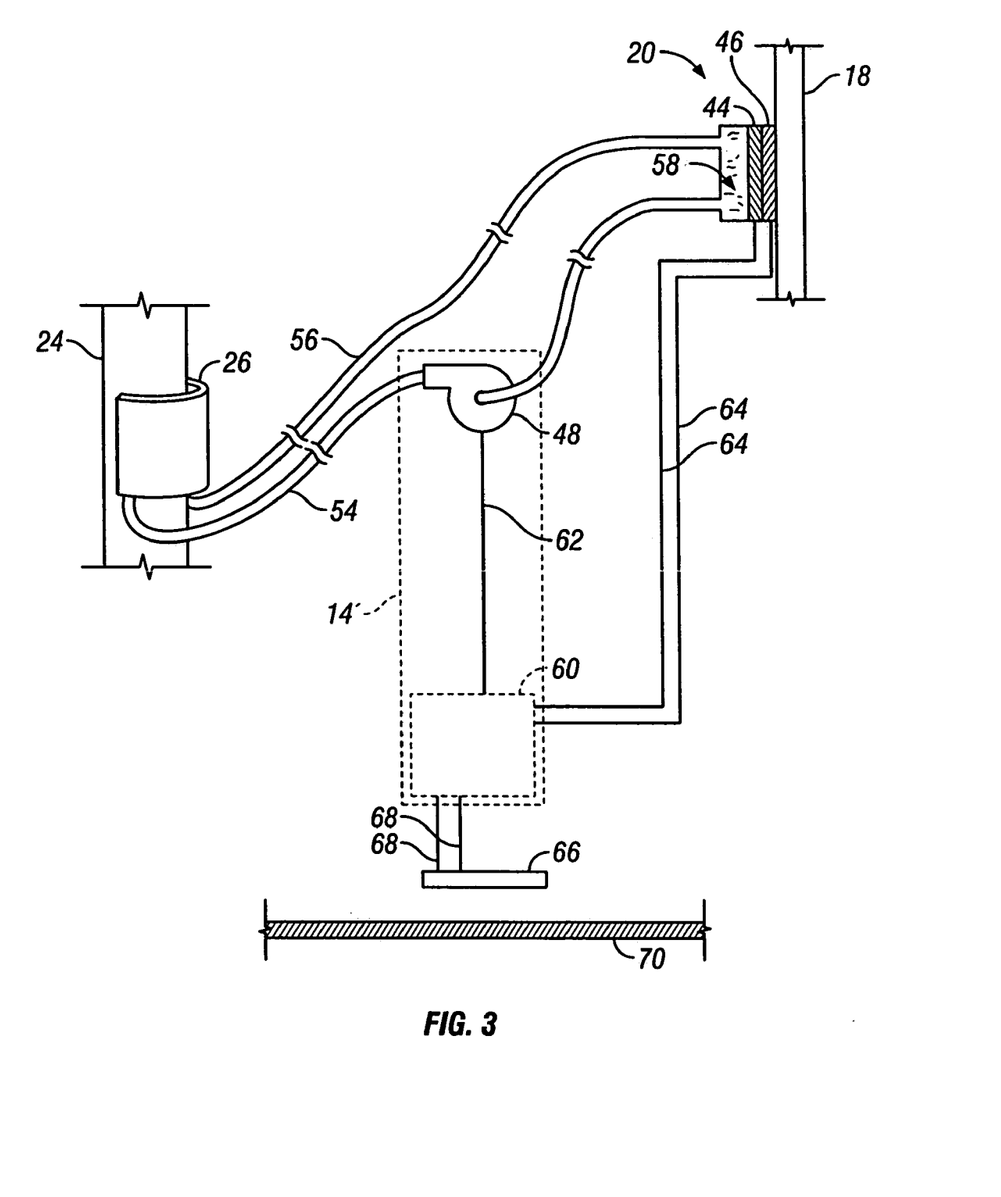
FIG. 3 shows a representative schematic of another variation on the cooling device with a pump and corresponding electronics.

FIG. 3 shows a representative schematic of another variation on the cooling device having a pump 48 and corresponding electronics in implantable unit 14'. Unit 14' may optionally be configured to have a power supply and/or control electronics 60 enclosed within the same housing. This unit 60 may be electrically connected via control line 62 to pump 48 to supply power and/or control the pump 48. Unit 60 is connected via control lines 64 to cooling unit 20 to each of heated and cooled regions 44, 46, respectively. Unit 60 may contain its own power supply or it may optionally be connected via electrical connection lines 68 to a charger 66 which may be subcutaneously implanted. Charger 66 is preferably placed below skin 70 such that an external charging unit (not shown) may be placed over skin 70 in the proximity of charger 66 such that unit 60 may be electrically charged thereby.

Figure 4A:
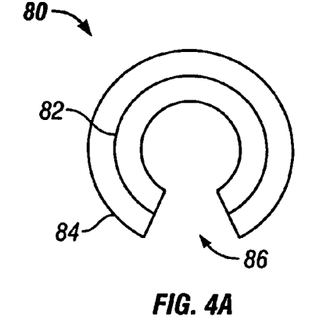
FIG. 4A shows a top view of a variation on the cooling element which preferably comprises a Peltier junction.
Figure 4B:
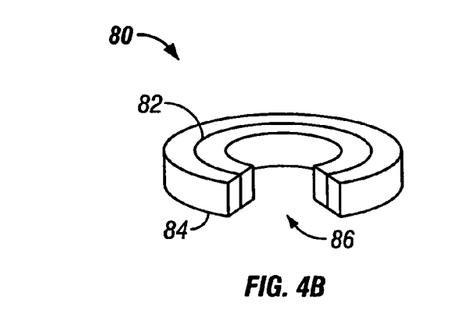
FIG. 4B shows an isometric view of the variation on the cooling element from FIG. 4A.

Aside from implantable unit 14, 14', or any other variations thereof, one variation of the cooling unit 20 is shown in FIGS. 4A and 4B. FIG. 4A shows a top view of circular junction 80 where it may be shaped in a semi-circular configuration where cooled region 82 is circumferentially surrounded by heated region 84. Both regions 82, 84 may define an opening 86 through which the vagus nerve 18 or other nerve body of interest may pass through to enable junction 80 to fixedly attach to the nerve. Junction 80 is preferably configured to be a size which is small enough to intimately attach to a nerve body, yet large enough to effect sufficient heat transfer to cool the nerve body temperature down by several degrees. As discussed above, a biocompatible adhesive which at least has a sufficient thermal conductivity, i.e., at least does not substantially impede the heat transfer or function as an insulator, may be used as a thermal interface between cooled region 82 and the nerve body. FIG. 4B shows an isometric view of junction 80 where opening 86 and the configuration of both regions 82, 84 may be clearly seen. The heat exchanger may be similarly configured to overlay junction 80 circumferentially or otherwise, but has been omitted for clarity.

Figure 5:
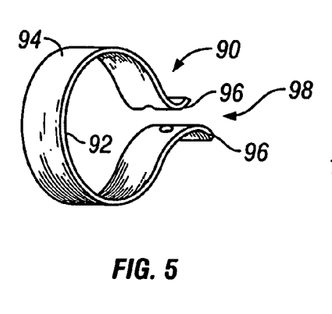
FIG. 5 shows a clamp variation of the cooling element.

FIG. 5 shows an isometric view of a clamp variation 90 of the cooling element. As shown, cooled region 92 may be positioned interiorly of heated region 94 in a manner similar to the variation shown in FIGS. 4A and 4B. The clamped junction 90 variation may have clamping members or arms 96 biased towards one another such that the tendency of clamping members 96 is to close opening 98. In use, members 96 may be urged open to allow for placement onto the nerve body. Once appropriately positioned, members 96 may be released to allow the junction 90 to securely fasten onto the nerve body.

Figure 6:
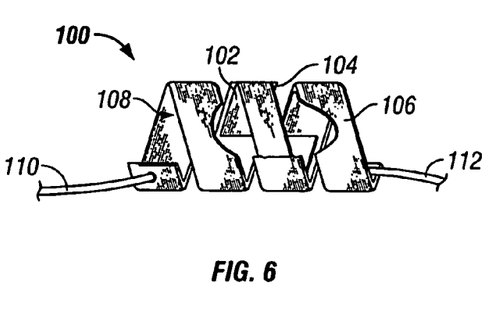
FIG. 6 shows a helical variation of the cooling element.

FIG. 6 shows a side view of a helical variation 100 of the cooling element. In this variation, cooled region 102 may be seen as being located interiorly of heated region 104. Surrounding heated region 104 is heat exchanger 106, shown partially removed to illustrate cooled and heated regions 102, 104, respectively. Leading to a first end of device 100 is feedline 110 through which fluid medium 58 may enter heat exchanger 106. At the opposing second end of device 100 is return line 112 through which fluid medium 58 may exit heat exchanger 106 once having absorbed the heat. Heat exchanger 106 may be helically formed as shown, or it may simply be configured as an overlaying layer through which the fluid medium 58 may flow therethrough. The device 100 is preferably flexible enough such that it may be unraveled temporarily by an external force to allow for placement around the nerve body. Upon releasing the external force, the device 100 may preferably reconfigure itself to reform opening 108 and wrap around the nerve body and reform the helical configuration. The helical shape may allow for efficient heat transfer from the nerve body to the device 100 given the surface contact area between the two bodies.

Figure 7:
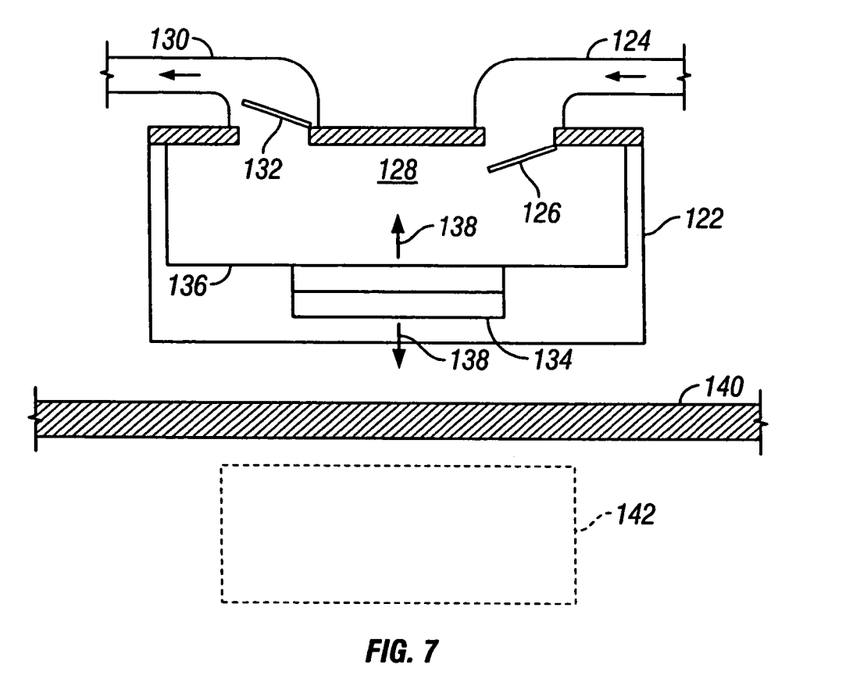
FIG. 7 shows an externally controllable variation on the pump.

Various conventional pumps 48 may be used in the cooling system to urge the fluid heat transfer medium 58 through the system from cooling unit 20 to heat exchanger 26. Although the pumps may be powered by power supplies located nearby, an implanted power supply may require periodic charging. One alternative method of removing the reliance on having to recharge power supplies, either invasively or non-invasively, is to utilize externally-driven pumping mechanisms. A variation of such a pump 120 is shown in FIG. 7. A cross-sectioned view of externally controllable and externally driven pump body 122 may be seen attached to fluid inlet line 124. The fluid medium may be transported via inlet line 124 through inlet valve 126 and into pumping chamber 128. From pumping chamber 128, the fluid medium may be forced out into outlet line 130 through outlet valve 132. Both inlet and outlet valves 126, 132, respectively, may be actively controllable or they may be conventional valves configured to maintain unidirectional flow of the fluid medium.

Because pump variation 120 does not require an implanted power supply, it may be implanted subcutaneously near skin 140. When pumping is to be actuated, an external alternating electromagnet 142 may be placed over skin 140 to activate actuator 134, which may comprise a permanent magnet, located next to pumping chamber 128 within pump 120. Actuator 134 is preferably attached to diaphragm 136 and when electromagnet 142 activates pump 120, actuator 134 may oscillate in the direction of arrows 138 at a controllable frequency to drive diaphragm 136, which in turn urges the fluid medium into and out of chamber 128. Alternating electromagnet 142 may be in a variety of forms, such as an externally held electromagnet which may be strapped into place when in use and removable when not in use.

Figure 8:
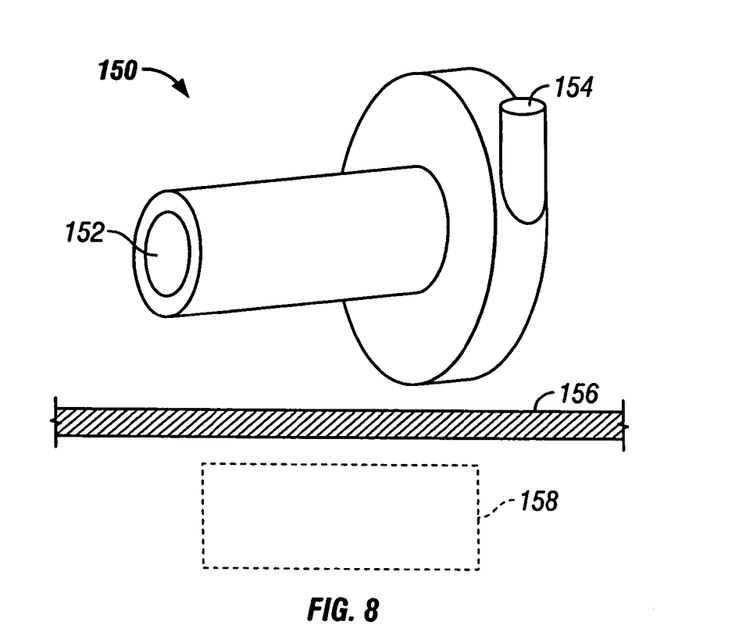
FIG. 8 shows an internally rotating variation on the pump.

FIG. 8 shows an alternative variation of the pump in rotational pump 150. Rotational pump 150 may also be implantable and may comprise a rotary pumping mechanism where the fluid medium may enter through inlet 152 and urged out through outlet 154. Rotational pump 150 may also be subcutaneously implanted beneath skin 156 such that access via an externally positioned alternating electromagnet 158 may be possible for actuating the pumping mechanism. Examples of rotational pump 150 may be seen in U.S. Pat. No. 5,840,070 to Wampler, which is incorporated herein by reference in its entirety.

The heat exchangers which may be in contact with the tubular body organs may be configured in a variety of ways. Functionally, a heat exchanger which maximizes the contact surface area between the exchanger and the body organ is desirable. Also, the exchanger is also preferably configured to hold onto the tubular body organ without damaging the tissue in any way. Thus, sharp edges and constrictive designs are undesirable.

Figure 9:
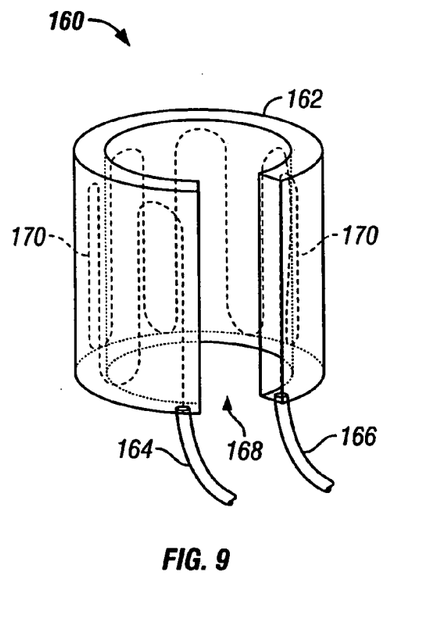
FIG. 9 shows a transparent isometric view of one variation on the heat exchanger cuff.
Figure 10:
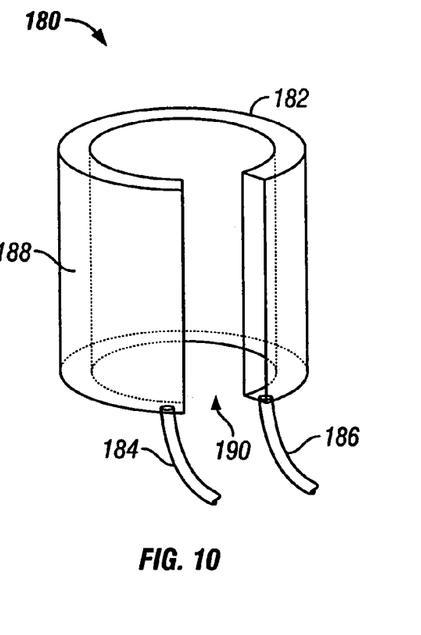
FIG. 10 shows a transparent isometric view of another variation on the heat exchanger cuff.

FIGS. 9 and 10 show transparent isometric views of two alternative heat exchanger cuff designs. Heat exchanger variation 160 shows cuff 162 having an inlet line 164, which may transport the heated (charged) fluid medium from the pump. The heat exchanger element 170 in this variation is configured into a looped or alternating manner to increase the surface area traversed by the fluid as it travels through cuff 162. Contact area 168 may thus optimize the heat transferred from the fluid medium into the tubular body organ through contact area 168. After the fluid medium has traversed through exchange element 170, it is then channeled out of cuff 162 through outlet line 166 to be returned to the nerve body to absorb more heat. Cuff 162 is preferably made from a biocompatible metal or alloy, e.g., stainless steel, nickel titanium, gold, platinum etc., which has a thermal conductivity value sufficient for transferring the heat from the fluid medium and through contact area 168. Metals or alloys which are poor heat conducting materials may be compensated by utilizing a larger contact area.

FIG. 10 shows heat exchanger variation 180 which may comprise cuff 182 attached to inlet and outlet lines 184, 186, respectively, and a contact area 190 similar to variation 160 shown in FIG. 9. However, variation 180 shows a single continuous heat exchange chamber 188 through which the fluid medium may fill before exiting through outlet line 186.

Figure 11:
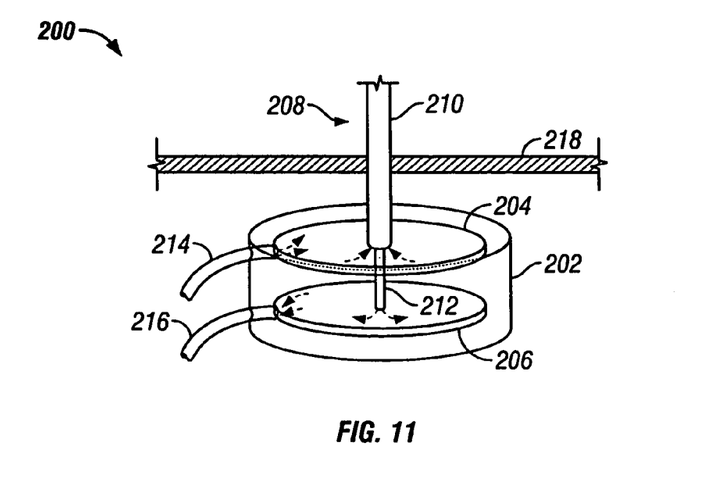
FIG. 11 shows an isometric view of a device for optionally injecting and aspirating coolant through the skin.

A combination pump and heat transfer device may alternatively be used in the cooling system, such as one shown in injectable pump 200 of FIG. 11. Injectable pump 200 is shown in this variation as a dual-chambered body 202 which may have an aspiration chamber 204 and an irrigation chamber 206 contained therein. Pump 200 is preferably implanted in the patient's body subcutaneously such that access to body 202 is possible by inserting a multi-lumened catheter 208 through skin 218. Catheter 208 preferably comprises an outer tubular structure 210 and an inner tubular structure 212, each of which preferably define access lumens therethrough. When the cooling system is to be actuated, catheter 210 may be inserted through skin 218 where the heated or charged fluid medium may be drawn into aspiration chamber 204 via inlet line 214 and up into outer tubing 210. Meanwhile, cooled fluid medium may be pumped or urged into irrigation chamber 206 via inner tubing 212 and into the system via outlet line 216. A positive or negative pressure pump may be fluidly connected to catheter 208 externally of the patient body to urge the fluid medium through the system. Alternatively, a syringe may be used to urge the fluid through the system. Multi-lumened catheter 208 may be separately insertable through skin 218, as described; alternatively, it may be permanently attachable to body 202 such that a proximal end of catheter 208 is maintained outside the patient's body and readily accessible when cooled fluid medium needs to be circulated through the system.

Figure 12A:
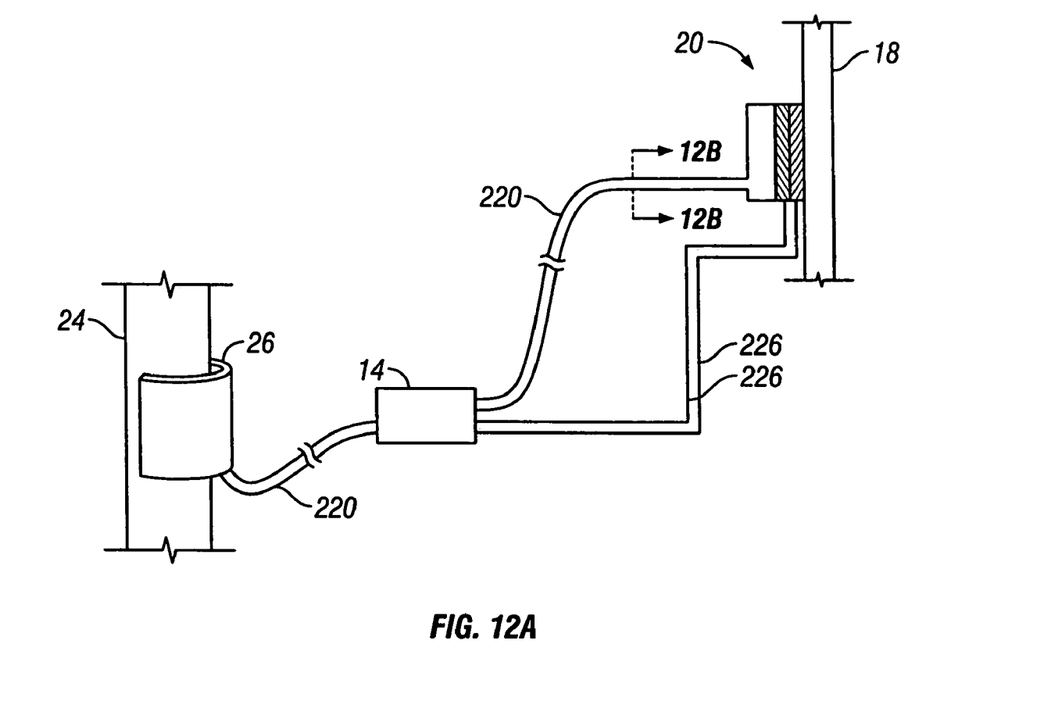
FIG. 12A shows a representative schematic of another variation on the cooling device having a single multi-lumened coolant tube.
Figure 12B:
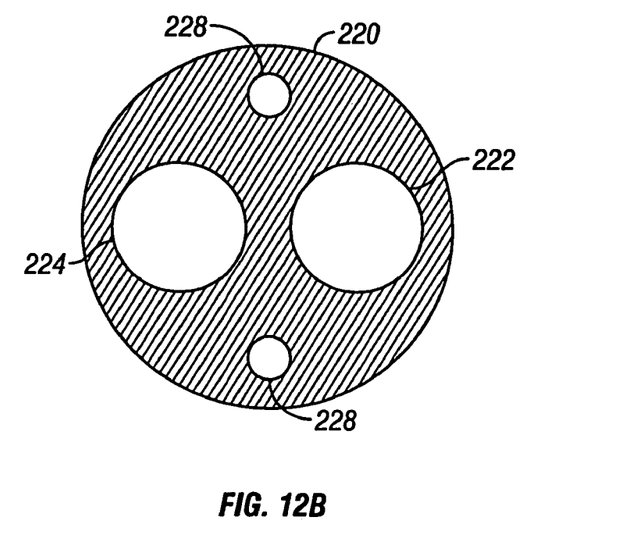
FIG. 12B shows cross-section 12B—12B from FIG. 12A of the variation on the multi-lumened coolant tube.

Although many of the variations above schematically illustrate at least two separate lines for transporting the fluid medium between heat sink and heat exchanger, they may be contained in a single multi-lumened line. As shown in FIG. 12A, a single multi-lumened line 220 may be used to fluidly connect heat exchanger 26 with cooling unit 20 through implantable unit 14. The electrical control lines 226 connecting implantable unit 14 with cooling unit 20 may also be contained within multi-lumened line 220 FIG. 12B shows a representative cross-sectioned view 12B—12B of line 220 taken from FIG. 12A. As seen, multi-lumened line 220 may define coolant line 222 and return line 224 through which the fluid medium may flow in opposing directions. To minimize the heat transferred between the two lines 222, 224 during flow, these lines are preferably insulated to attenuate any heat transfer from occurring therebetween. Multi-lumened line 220 may additionally define a number of access lumens 228 in which electrical, control, and/or power lines, e.g., control lines 226, may be contained within to minimize the number of separate lines running between units of the cooling system.

Because the lines connecting the various units of the cooling system may be implanted and routed through various parts of the body, some of the lines may undergo bending forces and stresses which may cause them to kink and stop the flow of the fluid medium therethrough. To prevent this from occurring, the lines may be reinforced by wrapping or surrounding them with various metals or alloys, as is well known in the catheter arts. Examples of such metals and alloys include stainless steels, nickel titanium (nitinol) alloys having superelastic alloy characteristics, and other superelastic alloys.

Figure 13:
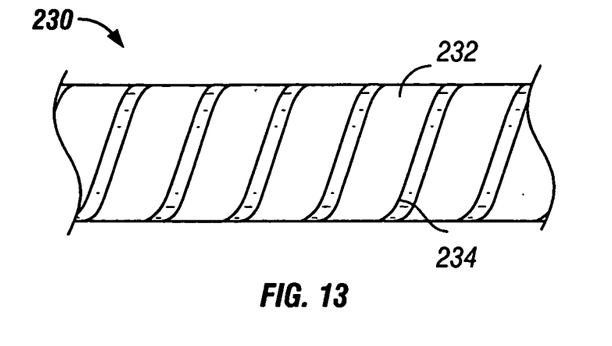
FIG. 13 shows a representative illustration of a coolant tube optionally wrapped with a metallic ribbon preferably having superelastic alloy characteristics.
Figure 14:
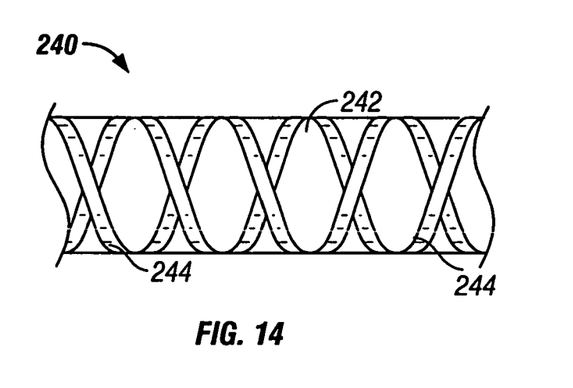
FIG. 14 shows a representative illustration of a coolant tube optionally braided with a metallic ribbon preferably having superelastic alloy characteristics.
Figure 15:
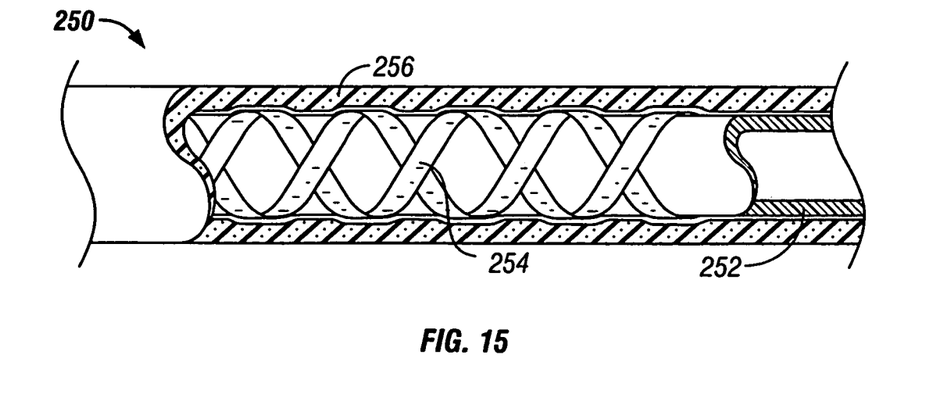
FIG. 15 shows a representative illustration of a coolant tube optionally covered with an insulative material.

FIG. 13 shows a representative side view of wrapped fluid line 230. As shown, fluid line 232 may be wrapped in a helical manner along at least a majority of its length by ribbon 234. Although a ribbon is shown as being used, a wire may also be used. FIG. 14 shows another variation in braided fluid line 240. In this variation, fluid line 242 may be wrapped in a braided manner by ribbon 244; wire may also be used to wrap line 242, or a combination of ribbon and wire may also be used. A further variation of a fluid line may be seen in FIG. 15, where insulated fluid line 250 may optionally be insulated with an exteriorly disposed tubular member 256. Although insulated fluid line 250 is shown with braided ribbon 254 disposed between fluid line 252 and insulation 256, the braided ribbon 254 may be disposed exteriorly of insulation 256, formed integrally within the walls of insulation 256, or even integrally within the walls of fluid line 252. The fluid lines may be made from a variety of conventionally extrudable or formable materials, e.g., silicone, polyethylene (PE), fluoroplastics such as polytetrafluoroethylene (PTFE), fluorinated ethylene polymer (FEP), perfluoroalkoxy (PFA), and thermoplastic polymers, such as polyurethane (PU), etc.

Figure 16:
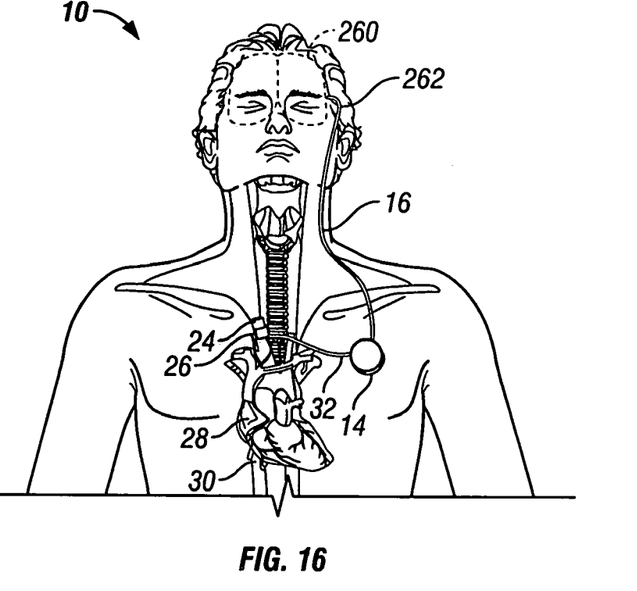
FIG. 16 shows a diagram of another variation of the cooling device implanted within a body and attached to the superior vena cava and a region within the brain.

Much of the discussion above has been related to the cooling of fibrous nerve bodies such as the vagus nerve. However, other applications of aspects of the present invention may also be utilized for the cooling of other regions within the body. FIG. 16 for instance shows a variation where a probe 262 may be used for implantation within the brain 260 of a patient. In this variation, probe 262 may employ a Peltier junction configured to be shaped as an elongate member for implantation within the brain 260. The elongate probe 262 may then be in contact with a heat exchanger in much the same manner as described herein to effect heat transfer away from the brain 260. Moreover, probe 262 or variations thereof may also be used for implantation within or adjacent to regions of the spinal cord to cool certain regions for the treatment of various maladies, e.g., chronic pain.

Figure 17:
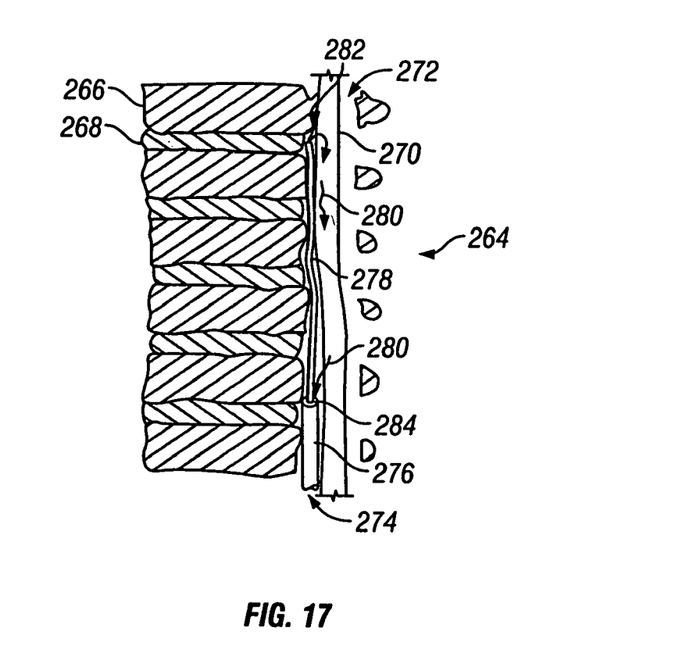
FIG. 17 shows a cross-sectioned portion of a vertebrae with a catheter inserted within the vertebral canal to cool a portion of the spinal column.

FIG. 17 shows a cross-sectioned portion of spinal column 264 through which a portion of spinal column 270 is held within vertebral canal 272. Spinal column 264 is comprised of vertebrae 266 and intevertebral discs 268. A catheter 276 having inner tubing 278 slidably disposed within outer tubing 276 may be inserted within a lower region of vertebral canal 272. Inner tubing 278 may be advanced up within vertebral canal 272 while holding outer tubing 276 in position relative to the patient. Once inner tubing 278 has been desirably positioned upstream within the cerebrospinal fluid, a cooling fluid, as described above, may be pumped out of distal end 282 of inner tubing 278 such that it flows downstream with the cerebrospinal fluid, as shown by arrows 280, while cooling the spinal column 270 as the fluid flows. When the fluid has reached outer tubing 276 downstream, the fluid that has been warmed by the surrounding cerebrospinal fluid and tissue may be drawn into lumen 284 of outer tubing 276. This spent fluid may be recycled and reinjected through catheter 276. Spinal column 264 may thus be cooled along its entire length or along portions by as little as, e.g., 2 to 3° C. below body temperature, to alleviate pain in a patient. The cooling fluid may be injected for as little as several minutes to as long as several hours at a time at an injection flow rate of, e.g., 5 to 10 cc/min, depending upon the particular condition of the patient. Alternatively, rather than directly injecting a fluid within the cerebrospinal fluid, a catheter which may be cooled along its entire length may also be inserted within vertebral canal 272 to cool spinal column 270.

The applications of the cooling devices and methods discussed above are not limited to fibrous nerve bodies, regions within the brain, or regions of the spinal cord but may include any number of further treatment applications. Other treatment sites may include areas or regions of the body such as organ bodies. Modification of the above-described assemblies and methods for carrying out the invention, and variations of aspects of the invention that are obvious to those of skill in the art are intended to be within the scope of the claims.

I claim:

1. An apparatus for reducing temperature within a body, comprising:
   a cooling element adapted to contact a first region within the body and reduce the temperature of the first region; and
   a heat exchanger thermally coupled to the cooling element and adapted to dissipate thermal energy from the cooling element via a second region of the body, the heat exchanger comprising a pump.

2. The apparatus of claim 1 wherein the heat exchanger is thermally coupled to the cooling element via at least one feedline.

3. The apparatus of claim 2 further comprising an additional feedline connected between the cooling element and the heat exchanger, wherein the feedline transfers the thermal energy from the cooling element to the heat exchanger via a fluid heat transfer medium, and wherein the additional feedline returns the fluid heat transfer medium after cooling to the cooling element.

4. The apparatus of claim 2 further comprising a thermally non-conductive insulator disposed at least partially over the feedline.

5. The apparatus of claim 2 wherein the feedline further comprises a ribbon disposed along at least a majority of a surface of the feedline.

6. The apparatus of claim 5 wherein the ribbon comprises a material selected from the group consisting of stainless steels and nickel titanium alloys.

7. The apparatus of claim 1 further comprising a fluid heat transfer medium between the cooling element and the heat exchanger.

8. The apparatus of claim 1 wherein the pump is adapted to be implanted within the body.

9. The apparatus of claim 1 wherein the pump has a motor which comprises an alternating magnet.

10. The apparatus of claim 1 wherein the cooling element comprises a Peltier junction.

11. The apparatus of claim 10 wherein the Peltier junction is in electrical communication with a power source.

12. The apparatus of claim 11 wherein the power source is located at a third region within the body.

13. The apparatus of claim 12 wherein the third region within the body is adjacent to a surface of the skin.

14. The apparatus of claim 1 wherein the first region within the body comprises at least one vagus nerve body.

15. The apparatus of claim 1 wherein the cooling element comprises a thermally conductive compliant clamp.

16. The apparatus of claim 1 wherein the cooling element is adapted to reduce the temperature of the first region to about 30° C.

17. The apparatus of claim 1 wherein the second region of the body comprises a tubular organ body having a blood flow therethrough sufficient to dissipate the thermal energy.

18. The apparatus of claim 17 wherein the tubular organ body comprises a superior vena cava or an inferior vena cava organ body.

19. The apparatus of claim 1 wherein the second region of the body comprises a location adjacent to a surface of the skin.

20. A method for reducing temperature within a body, comprising:
   cooling a first region within the body from a first temperature to a second lower temperature via a cooling element;
   dissipating thermal energy from the cooling element into a second region within the body; wherein dissipating thermal energy comprises pumping.

21. The method of claim 20 wherein cooling the first region comprises cooling at least one vagus nerve body.

22. The method of claim 20 wherein cooling the first region comprises cooling tissue via a Peltier junction in intimate contact with the first region.

23. The method of claim 20 wherein cooling the first region comprises cooling to the temperature of about 30° C.

24. The method of claim 20 wherein dissipating thermal energy comprises transferring the thermal energy from the cooling element to the second region.

25. The method of claim 24 wherein transferring the thermal energy comprises pumping a fluid heat transfer medium from the cooling element to the second region via a pump implanted at a third region within the body.

26. The method of claim 25 wherein pumping the fluid heat transfer medium comprises transcutaneously exposing the pump to an alternating electromagnetic field to actuate the pump.

27. The method of claim 20 wherein dissipating thermal energy comprises passing the thermal energy via a heat exchanger into the second region.

28. The method of claim 27 wherein passing the thermal energy comprises passing the thermal energy into a tubular organ body having a blood flow therethrough sufficient to dissipate the energy.

29. The method of claim 28 wherein passing the thermal energy into the tubular organ body comprises passing the thermal energy into a superior vena cava or an inferior vena cava organ body.

30. The method of claim 20 wherein dissipating thermal energy comprises dissipating the thermal energy into the second region at a location adjacent to a surface of the skin.

31. An apparatus for reducing temperature within a body, comprising:
   a cooling element adapted to contact a first region within the body and reduce the temperature of the first region, the cooling element comprising a Peltier junction; and
   a heat exchanger thermally coupled to the cooling element via at least one feedline and adapted to dissipate thermal energy from the cooling element via a second region of the body.

32. The apparatus of claim 31 further comprising an additional feedline connected between the cooling element and the beat exchanger, wherein the feedline transfers the thermal energy from the cooling element to the heat exchanger via a fluid heat transfer medium, and wherein the additional feedline returns the fluid heat transfer medium after cooling to the cooling element.

33. The apparatus of claim 31 wherein the Peltier junction is in electrical communication with a power source.

34. The apparatus of claim 33 wherein the power source is located at a third region within the body.

35. The apparatus of claim 34 wherein the third region within the body is adjacent to a surface of the skin.

* * * * *